US00PP08426P

United States Patent [19]

Jessel, Jr.

[11] Patent Number: Plant 8,426

[45] Date of Patent: Oct. 19, 1993

[54] CARNATION PLANT NAMED CFPC SCORE

[75] Inventor: Walter H. Jessel, Jr., Salinas, Calif.

[73] Assignee: California Florida Plant Co., L.P., Salinas, Calif.

[21] Appl. No.: 976,136

[22] Filed: Nov. 10, 1992

[51] Int. Cl.[5] ..... A01H 5/00

[52] U.S. Cl. ..... Plt./70.2

[58] Field of Search ..... Plt./70.1, 70.2, 70.3

[56] References Cited

U.S. PATENT DOCUMENTS

P.P. 4,100 9/1977 Euser ..... Plt. 70.2

*Primary Examiner*—Howard J. Locker

*Attorney, Agent, or Firm*—Christie, Parker & Hale

[57] ABSTRACT

A new carnation plant producing flowers of white and striped purple coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC Score'.

Among the novel combination of characteristics possessed by the new variety which distinguishes it are flowers of the attractive white and striped purple flower coloring which tend to be less sensitive to thrip than the cultivar known as 'APACHE' (U.S. Plant Pat. No. 4,100).

Asexual reproduction by propagation by side shoot cuttings of the new variety as performed in Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Score'.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plant numbers in the aforementinoed color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Phenotypic expression may vary depending on light and cultural conditions.

Name: 'CFPC Score'.

Classification:

*Botanical.*—*Dianthus caryophyllus.*

*Commercial.*—Carnation, spray type.

Parentage:

*Female parent.*—Unnamed seedling (No. 870914).

*Male parent.*—Unnamed seedling (No. 870642).

Plant:

*Height.*—About 32 inches.

*Growing habit.*—Herbaceous, semi-upright.

*Blooming habit.*—Terminal as a spray.

*Blooming season.*—Year-round.

*Rooting time.*—About 15 days.

*Mutation prone.*—Does not appear to be.

*Disease Resistance.*—Average.

*Breaking action.*—Good.

Foliage:

*Color.*—Upper side: Near 139A. Lower side: Near 141A.

*Size.*—About 5½ inches at base of plant.

*Quantity.*—Numerous.

*Shape.*—Lanceolate.

*Texture.*—Smooth.

*Ribs.*—Central, keeled.

*Arrangement.*—Bilaterial along stem.

*Stem color.*—Green.

Bud:

*Shape.*—Oval.

*Color.*—Green.

*Length.*—About 1½ inches.

*Diameter.*—About ½ inch.

Calyx:

*Number of sepals.*—About 5.

*Length.*—About 1 inch.

*Width.*—About ⅛ inch.

*Color.*—Outside — near 143A. Inside — near 144D.

Bloom:

*Shape.*—Round.

*Size.*—Diameter average: About 2 inches. Depth average: About 1 inch.

*Borne.*—Terminal as a spray.

*Color.*—General tonality: White with purple stripes. Upper side: Near to 62D (fading to white) with near 74B stripes. Lower side: Near 65D fading to white. Center: Near 65D fading to white.

*Fragrance.*—Slight.

Petals:

*Number.*—About 52.

*Outer petals.*—Length: About 1 inch. Width: About 1 inch.

*Central petals.*—Length: About ½ inch. Width: About ⅓ inch.

*Texture.*—Smooth.

*Form.*—Fan-shaped.

*Appearance.*—Shiny.

Reproductive organs:

*Stamens.*—Number: About 10. Arrangement: Around the ovary.

*Anthers.*—Length: About ⅛ inch. Color: Near 158A.

*Filaments.*—Length: About 1 inch. Color: Near 155D.

*Pistil.*—Number: About 3. Color: Near 155D.

*Stigma.*—Number: About 3. Color: Near 155D.

*Ovary.*—Shape: Conical. Color: Base — green. Body — green. Apex — tan.

*Fertility.*—Male — poor. Female — good.

I claim:

1. A new and distinct variety of carnation plant, substantially as shown and described.

* * * * *

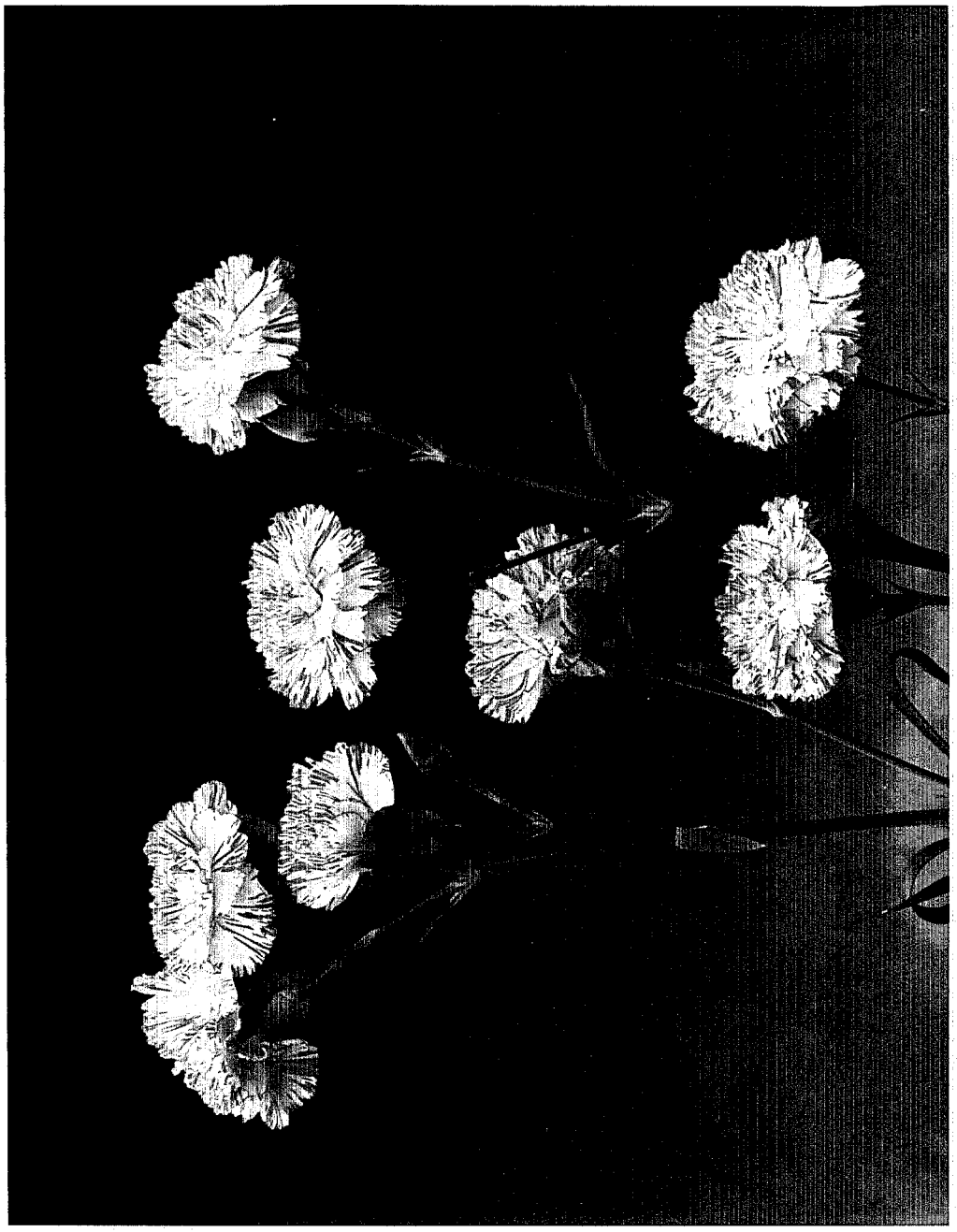

UNITED STATES PATENT AND TRADEMARK OFFICE

CERTIFICATE OF CORRECTION

PATENT NO. : Plant 8,426

DATED : October 19, 1993

INVENTOR(S) : CARNATION PLANT NAMED CFPC SCORE

It is certified that error appears in the above-indentified patent and that said Letters Patent is hereby corrected as shown below:

Column 1, line 36, change "plant numbers" to
-- plate numbers --.

Signed and Sealed this

Twenty-first Day of June, 1994

*Attest:*

Bruce Lehman

BRUCE LEHMAN

*Attesting Officer*

*Commissioner of Patents and Trademarks*